(12) United States Patent
Cui et al.

(10) Patent No.: US 7,850,771 B2
(45) Date of Patent: Dec. 14, 2010

(54) EMULSION COMPOSITIONS FOR WOOD PROTECTION

(75) Inventors: Futong Cui, Charlotte, NC (US); Alan F. Preston, Charlotte, NC (US)

(73) Assignee: Viance, LLC, Charlotte, NC (US)

( * ) Notice: Subject to any disclaimer, the term of this patent is extended or adjusted under 35 U.S.C. 154(b) by 1240 days.

(21) Appl. No.: 11/222,552

(22) Filed: Sep. 9, 2005

(65) Prior Publication Data

US 2006/0057300 A1   Mar. 16, 2006

Related U.S. Application Data

(60) Provisional application No. 60/608,674, filed on Sep. 10, 2004.

(51) Int. Cl.
| | |
|---|---|
| *C09D 5/14* | (2006.01) |
| *C09D 5/16* | (2006.01) |
| *C09K 15/16* | (2006.01) |
| *C09K 15/18* | (2006.01) |

(52) U.S. Cl. .................. 106/15.05; 106/16; 106/17; 106/18.21; 252/380; 252/401; 252/402; 252/403; 252/405

(58) Field of Classification Search ............. 106/18.21; 252/401
See application file for complete search history.

(56) References Cited

U.S. PATENT DOCUMENTS

| | | | |
|---|---|---|---|
| 4,496,613 A | | 1/1985 | Zagefka et al. |
| 4,542,146 A | * | 9/1985 | Van Gestel et al. ........... 514/383 |
| 4,954,338 A | * | 9/1990 | Mattox ........................ 514/372 |
| 5,013,748 A | | 5/1991 | Radtke et al. |
| 5,536,305 A | * | 7/1996 | Yu ............................ 106/18.33 |
| 5,827,522 A | * | 10/1998 | Nowak ........................ 424/405 |
| 5,874,025 A | * | 2/1999 | Heuer et al. ................. 252/383 |
| 5,880,143 A | * | 3/1999 | Goettsche et al. ........... 514/383 |
| 6,274,199 B1 | * | 8/2001 | Preston et al. ............... 427/298 |
| 6,348,089 B1 | * | 2/2002 | Marx et al. ................. 106/18.32 |
| 6,423,307 B2 | | 7/2002 | Saettone et al. |
| 6,464,764 B1 | | 10/2002 | Lichtenberg et al. |
| 6,558,685 B1 | * | 5/2003 | Kober et al. ................. 424/405 |
| 6,641,927 B1 | | 11/2003 | Honary |
| 6,686,056 B2 | | 2/2004 | Roos et al. |
| 7,297,193 B1 | * | 11/2007 | Ashmore et al. .......... 106/18.29 |
| 2003/0060504 A1 | * | 3/2003 | Yoshida et al. ............... 514/460 |
| 2003/0108759 A1 | | 6/2003 | Roos et al. |
| 2004/0011244 A1 | * | 1/2004 | Cui et al. ....................... 106/2 |
| 2005/0132926 A1 | * | 6/2005 | Cui et al. .................. 106/18.29 |
| 2006/0057300 A1 | * | 3/2006 | Cui et al. ..................... 427/440 |
| 2008/0187669 A1 | * | 8/2008 | Kingma et al. .............. 427/342 |

FOREIGN PATENT DOCUMENTS

| | | |
|---|---|---|
| EP | 0148526 A | 12/1984 |
| WO | WO 00/71313 A | 11/2000 |
| WO | WO 00/71314 A | 11/2000 |
| WO | WO 02/76696 A | 3/2002 |

OTHER PUBLICATIONS

Joseph, "Is Benzyl Alcohol a VOC?", Ask the Expert Question-and-Answer Archive, PCRC Paints & Coatings Resource Center, Nov. 2005, http://www.paintcenter.org/rj/nov05o.cfm, printed Aug. 17, 2009.

"Benzyl Alcohol Paint Stripping", Joint Service Publication Prevention Opportunity Handbook, http://205.153.241.230/P2_Opportunity_Handbook/5_9.html, printed Aug. 17, 2009.

Australian Patent Office, Examiner's First Report on Patent Application No. 2005284978, dated May 11, 2010.

* cited by examiner

*Primary Examiner*—Joseph D Anthony
(74) *Attorney, Agent, or Firm*—McAndrews, Held & Malloy, Ltd.

(57) ABSTRACT

There are provided compositions for the preservation of wood and related cellulosic and lignocellulosic materials. The wood preservative compositions of the present invention contain an organic preservative agent and an organic acid, and can be solubilized in an organic phase essentially free of volatile organic compounds (VOC). The organic acids may serve various purposes in the compositions of the present invention: (1) increased preservative solubility in the organic phase, (2) improved distribution gradient of the active preservative in treated wood, or (3) reduction of preservative leaching.

51 Claims, No Drawings

EMULSION COMPOSITIONS FOR WOOD PROTECTION

CROSS-REFERENCE TO RELATED APPLICATIONS

Priority is claimed from provisional application U.S. Ser. No. 60/608,674, filed Sep. 10, 2004. The entire specification and all the claims of the provisional application referred to above are hereby incorporated by reference to provide continuity of disclosure.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

When left untreated, wood becomes subject to degradation by a variety of natural causes. The wood preservation process deposits or fixes chemical preservatives in the wood, and the toxic nature of the chemicals effectively prevents the attack of living organisms on the wood, preserving structural integrity and thereby extending the lifetime of the treated wood. In general, the wood preservation formulations desirably have the following characteristics: be toxic to attacking organisms; be able to penetrate wood; be chemically stable; be safe to handle; be economical to use; not weaken the structural strength of the wood; and not cause significant dimensional changes within the wood.

Traditional chemicals used for wood treatment are generally divided into two major groups: (i) organics—these are oil-borne chemical formulations, consisting of an organic preservative dissolved in a suitable petroleum oil carrier and (ii) inorganics—these are water-borne chemical formulations, consisting of inorganic compounds dissolved in water as a carrier. The most common wood preservatives include water-soluble inorganic metal salts that are supplied with or without co-biocides. These include Chromated Copper Arsenate (CCA), Ammoniacal Copper Arsenate (ACA), Alkaline Copper Quat (ACQ), Copper Azole (CA) and various forms of borates. These inorganic preservatives are inexpensive and do not require costly formulating agents. For example, CCA is completely water-soluble and requires no formulating agents, and alkaline copper based preservatives such as ACQ require only a complexing agent, such as ammonia or monoethanolamine, to ensure solubility of the copper component and to help chemical fixation in the treated wood.

Although Chromated Copper Arsenate (CCA), previously the most commonly used preservative, has been effective and economical, changing market perceptions and the public interest in alternative preservatives has led to changes in the treated wood products offered to consumers at retail. In consultation with the Environmental Protection Agency, manufacturers have made a transition to alternative wood preservatives for the residential and outdoor market. The wood treating industry voluntarily agreed to phase out CCA for residential applications at the end of 2003, although CCA is still approved for use in certain commercial applications. Residential applications include fencing, decks, picnic tables, playground equipment, and other construction projects that come into regular human contact in residential areas. Commercial applications include docks in salt or brackish water, boat construction, shakes and shingles, plywood flooring, laminated beams, highway barriers, agricultural timbers and poles, and similar projects.

As a result of withdrawing CCA for many applications, a renewed interest in the use of organic preservatives alone or in combination with co-biocides has occurred. These organic preservatives are highly effective fungicides having very low mammalian and aquatic toxicity. Due to their low solubility in water, organic biocides, excepting some quaternary ammonium compounds, are used in combination with organic solvents to form solutions, suspensions, or emulsions. Emulsions include conventional emulsions (macro-emulsions), micro-emulsions, or emulsifiable concentrates. To produce preservative emulsions, micro-emulsions, or emulsifiable concentrates, organic preservatives have been dissolved in organic solvents and mixed with various emulsifiers.

U.S. Pat. No. 4,954,338, European Patent Application 0148526, European Patent 0148526, and U.S. Pat. No. 5,536,305 disclose water dilutable formulations in which isothiazolone and triazole preservatives are dissolved in various organic solvents and mixed with emulsifiers.

In European Patent 0148526, commonly used emulsifiers such as ethoxylated phenol derivatives and ethoxylated oils are described as solubilizers for the active preservatives. The use of synthetic and natural resins and oils, such as drying oils, to improve the applicability and chemical/physical stability of the formulations is discussed.

WO 02/076696 discloses emulsifier free compositions containing a modified alkyd resin, solvent, preservative and water. In this disclosure, the preservative solution in organic solvent is emulsified by the acrylic acid modified alkyd resin, which serves as an emulsifier. The particle size and long-term stability of the resulting emulsion is not discussed.

Of concern regarding the use of organic preservatives is the limited stability of suspensions and the need for organic solvents, which are expensive, difficult to handle due to their flammable or combustible nature, and are environmentally sensitive due to volatile organic compound (VOC) emissions and potential toxicity.

An additional concern in the use of organic preservatives is fixation and depletion. While most inorganic preservatives are "fixed" in the treated wood through a combination of chemical reactions, physical interactions, and precipitation, most organic preservatives have limited chemical and physicochemical interactions with wood. Although most organic preservatives have low water solubility, normally in the part per million (PPM) range, preservative depletion is significant under in-service conditions. It has been estimated that certain organic preservatives could lose more than 20% of the original loading after only one year of aboveground field exposure (F. Cui, 2002, unpublished results). Another concern when using organic preservative compositions is a poor distribution gradient that is unsuitable for preventing decay. Some organic preservatives can have such a steep distribution gradient that the center of the treated wood does not have adequate preservative loading to prevent decay, even though the outer layer has more than adequate preservative loadings. In contrast, inorganic preservatives such as CCA do not usually have prohibitive distribution gradients at concentrations typically used, i.e. the chemical concentration difference in the outer and inner layers of the treated wood is insignificant.

The use of acids in wood preservative formulations has been described in the patent literature. For example, EP 0 402 697 describes mixtures of fenpropimorph and water-insoluble acids. Mixtures of amines and acids are described in DE-A-3 736 298. U.S. Pat. No. 5,880,143 describes triazole based compositions containing tertiary amines and dicarboxylic acids in the presence of optional monocarboxylic acids such as 2-ethylhexanoic acid. The main purpose of using the carboxylic acids, in combinations with amines, seems to be corrosion resistance and formulation stability. In addition, U.S. Pat. No. 5,880,143 requires the use of water-soluble or water miscible organic solvents. Carboxylates are used as counter ions for quaternary ammonium compounds in U.S. Pat. No. 5,013,748. U.S. Pat. No. 5,013,748 describes compositions containing at least one triazole, a benzimidazole, and at least one quaternary ammonium compound dissolved in an ether type solvent as well as a carboxylic acid in the presence of optional oils and fixatives. Acids described in U.S. Pat. No. 5,013,748 included formic acid, acetic acid, and propionic acid. The purpose of these low molecular weight acids is not discussed. Sustained release antifungal formulations containing polyacrylic acid and triazole derivatives are described in U.S. Pat. No. 6,423,307. Polyacrylic acid is described as a bioadhesive to improve bioavailability of the active fungicide.

Solvent-free compositions based on quaternary ammonium compounds (U.S. Pat. No. 6,464,764) and amine oxides as solubilizers (WO 00/71314, WO 00/71313) have been described. Tests (unpublished results) suggested that the use of high levels of fungicidally active quaternary ammonium compounds did not significantly contribute to the efficacy of triazole type organic preservatives. In addition, the presence of quaternary ammonium compounds poses compatibility problems with most emulsion water repellents. Quaternary ammonium compounds and amine oxides require long hydrocarbon chains to provide water repellency. Formulations containing these long chain amine oxides or quaternary ammonium compounds are difficult to handle due to their high viscosity.

Drying oils (U.S. Pat. No. 6,641,927) and oxidatively drying polybutadiene polymers containing quaternary ammonium functions (U.S. Pat. No. 4,496,613) have been described for preservative compositions. In U.S. Pat. No. 6,641,927, neat soybean oil was described for use to impregnate wood. See also U.S. Pat. No. 6,686,056; U.S. Publ. Appl. No. 2005/003190; and U.S. Publ. Appl. No. 2003/0108759 disclosing reactive oil/copper preservative systems for wood products.

BRIEF SUMMARY OF THE INVENTION

The present invention provides compositions for the preservation of wood and related cellulosic and lignocellulosic materials. The wood preservative compositions of the present invention contain an organic preservative agent and an organic acid, solubilized in an organic phase essentially free of volatile organic compounds (VOC).

BRIEF DESCRIPTION OF SEVERAL VIEWS OF THE DRAWINGS

[Not Applicable]

DETAILED DESCRIPTION OF THE INVENTION

The present invention provides wood preservative compositions containing an active organic preservative solubilized in a VOC-free organic phase containing an organic acid. The compositions of the present invention can be formulated, in the presence of an emulsifier, as water-dilutable emulsion concentrates or emulsifiable concentrates.

The inventors contemplate that any organic preservatives can be used. Exemplary organic preservatives of the invention include 3-Iodo-2-propynyl butyl carbamate, chlorothalanil, quaternary ammonium compounds, isothiazolones such as 4,5-dichloro-2-n-octyl-4-isothiazolin-3-one, triazoles, or a combination of these. Exemplary triazole organic preservatives of the present invention include Propiconazole, Tebuconazole, Hexaconazole, Cyproconazole, Dinaconazole, or a combination of these. Optionally, an active biocide such as an insecticide, fungicide or a mold inhibitor can be added, at a concentration which depends on the type of actives as well as the application. Exemplary concentrations of the active preservative are 0.1-30 weight %, more preferably 0.5-20 weight %, based on the weight of the formulation. Broadly speaking, any amount of an active preservative effective to preserve wood is contemplated. The inventors contemplate that any organic acid can be used. Exemplary organic acids of the invention include a carboxylic acid, a sulfonic acid, a phosphonic acid, or a combination of these. Exemplary carboxylic acids include oleic acid, linoleic acid, linolenic acid, an acid combination derived from a natural oil such as linseed fatty acid or soy fatty acid, 2-ethylhexanoic acid, benzoic acid, acrylic acid, methacrylic acid, or a combination of these. Exemplary acids are polymerizable, containing carbon-carbon double bonds. One example of a sulfonic acid includes dodecylbenzenesulfonic acid. The concentration of the acids can be 0.1-15%, more preferably 0.5-10%, based on the weight of the formulation.

The organic acid may serve one or more of the following purposes in the compositions of the present invention: (1) increasing preservative solubility in the organic phase, (2) improving the distribution gradient of the active preservative in treated wood, and (3) reducing preservative leaching.

The organic phase of the invention may comprise a hydrophobe. Exemplary concentrations of the hydrophobe component are 0-40 weight %, and more preferably 10-30 weight %, based on the weight of the total formulation. The hydrophobe is more preferably a strong hydrophobe. Exemplary strong hydrophobes include waxes, such as petroleum waxes, natural waxes, synthetic waxes, or a combination of these. Exemplary petroleum waxes include slack wax or microcrystalline wax. Exemplary natural waxes include bees' wax or carnauba wax. Exemplary synthetic waxes include polyethylene wax or oxidized polyethylene wax. Preferred waxes have a melting point of 30-100° C., most preferably in the range of 40-60° C. The most preferred wax is a slack wax having a melting point of 45-60° C. and an oil content of 5-20%. The wax component of the current invention includes those that provide good water repellency to wood and wood products.

The wood preservative compositions of the present invention can further comprise an emulsifier, and can be in the form of ready to use emulsions or emulsifiable concentrates. The type and use level of the emulsifiers depend on the nature of the organic phase as well as the form of the formulation. Conventional emulsions (macro-emulsions) need less emulsifiers than micro-emulsions and emulsifiable concentrates. Emulsifiers useful in the present invention include non-ionic, anionic, cationic, and amphoteric surfactants, and combinations thereof. Non-ionic surfactants that may be used include, for example, ethoxylated nonylphenol, ethoxylated alcohol, ethoxylated organic acid, ethoxylated castor oil, or a combination of these. Useful ethoxylated castor oils include those having an HLB of at least 12. Examples of useful anionic surfactants include salts of dodecylbenzensulfonic acid. Emulsifiers containing polymerizable functional groups can be used. In addition, the wood preservative compositions of the present invention can further comprise an agent to increase the solubility of the preservative. The preservative solubility-enhancing agent is generally present in an amount effective to increase the solubility of the preservative in the organic phase. Exemplary preservative solubility-enhancing agents include alkyd resins, natural oils, chemically modified oils, hydrocarbon resins, synthetic compounds such as esters, or a combination of these. Examples of suitable natural oils include linseed oil, tung oil, fish oil, or a combination of these. The most preferred natural oils are the drying oils such as linseed oil which can cross-link through air oxidation.

Another class of solubility enhancing agents of the current invention is chemicals of moderate polarity, which offer good solubility for the active organic preservatives and at the same time offer good compatibility with the rest of the components of the organic phase. The most preferred esters are polymerizable acrylic or methacrylic esters having low vapor pressure and high flash point, such as butyl acrylate, butyl methacrylate, hexyl acrylate, hydroxyethyl methacrylate, or ethyleneglycol dimethacrylate. Free radical initiators, including thermo-cleavable initiators such as AIBN (2,2'-azobisisobutyronitrile) and potassium persulfate, or redox initiators such as ferrous sulfate/hydrogen peroxide are required to polymerize the esters in the treated wood. When a thermo-cleavable initiator such AIBN is used as an initiator, polymerization is achieved at the same time as the wood is dried in a kiln after treatment. Alternatively, polymerization can be initiated by radiation.

Hydrocarbon resins have been used in solvent-based wood preservative formulations. Examples are the rosin esters from Arizona Chemical Company in Panama City, Fla. and Escorez series resins from ExxonMobil. These resins can moderately increase the solubility of organic preservatives in the organic phase and reduce the leaching rate from the treated wood.

Examples of synthetic compounds include those with moderate polarity such as esters, ketones, and ethers. Synthetic compounds with medium polarity suitable for use in the present invention include for example polymerizable acrylic esters, polymerizable methacrylic esters, or a combination of these. Polymerizable acrylic esters used as preservative solubility-enhancing agents in the present invention include for example butyl acrylate, hexyl acrylate, or a combination of these. Useful polymerizable methacrylic esters include butyl methacrylate, hydroxyethyl methacrylate, ethyleneglycol dimethacrylate, or a combination of these.

When a natural oil or alkyd resin is used as the solubility-enhancing agent, the most preferred acid is an unsaturated natural acid or mixture, since the acids are cross-linked under the same conditions as the solubility enhancing agents. When unsaturated esters such as acrylates and methacrylates are used as the solubility enhancing agents, the most preferred acids are acrylic or methacrylic acid. The concentration of these polymerizable acids preferably is 0.1-15%, more preferably 0.5-10%, based on the weight of the formulation.

The solubility-enhancing agents described above may constitute, for example, 0.1-40 weight %, more preferably 5-30 weight %, based on the total weight of the formulation. When a drying oil is used as a solubility-enhancing agent, a catalyst such as a cobalt or manganese soap can be optionally added in the formulation. These soaps can be conveniently formed in situ by reacting a carbonate, hydroxide, or oxide of the corresponding metal with a carboxylic acid. The preferred concentration of metal is 0.001 weight %-0.4 weight %, based on the weight of the drying oil. When a polymerizable ester is used as the solubility-enhancing agent, the molar ratio of the ester to radical initiators, such as AIBN, is preferably 500:1 to 5000:1.

The solubility-enhancing agent can serve both as a solubilizing medium and as a water repellent. The cross-linked drying oil or synthetic ester increases the fixation of the preservative in the wood matrix and also contributes to the water repellency of the treated wood. The drying oil or alkyd resin component of the present wood preservative composition can undergo cross-linking by air oxidation, in the presence or absence of a catalyst. When an acrylic or methacrylic ester is used as the solubility-enhancing agent, cross-linking can be achieved by a radical initiator.

The combined use of wax, solubility enhancing agents, and organic acids provide the benefits of excellent water repellency, low preservative leaching, a relatively flat preservative distribution gradient, and an organic phase essentially free of VOC.

The wood preservative composition of the present invention can further comprise a free radical initiator. The free radical initiator can be a thermo-cleavable initiator, a redox initiator, or a combination of these. Examples of suitable thermo-cleavable initiators include AIBN (2,2'-azobisisobutyronitrile), potassium persulfate, or a combination of these. Suitable redox initiators can include for example a combination of ferrous sulfate and hydrogen peroxide. From about 0.01% to about 1% by weight of a free radical initiator can be used, for example.

In addition, the wood preservative composition of the present invention can further have a small molecular weight (Molecular weight<200) nitrogen-containing compound. The nitrogen-containing compound is preferably present at a concentration effective for improving the chemical distribution gradient in a treated wood product. Exemplary nitrogen-containing compounds include compounds such as 1,2,4-triazole.

The wood preservative composition of the present invention can also comprise an efficacy enhancing active ingredient. Exemplary efficacy enhancing active ingredients include organic biocides. Examples of organic biocides include insecticides, fungicides, mold inhibitors, or a combination of these. Suitable insecticides can include Imidacloprid, Cyfluthrin, or a combination of these. Exemplary concentrations of fungicides include 0.01-30%, more preferably 0.5-20% based on the weight of the formulation. The concentration of the insecticide and mold inhibitor depends on the type of actives as well as the application.

A metal such as zinc (II), copper (II), cobalt (II), and manganese (II) in the form of a carbonate, hydroxide, or oxide can also be added to the formulation of the present invention to form a metal carboxylate through an in situ reaction with the carboxylic acid. These metal carboxylates, commonly referred to as metal soaps, could act as cross-linking catalysts for the drying oils or alkyd resin. The addition of metals to the formulation enhances the water repellency of the treated wood. A useful concentration of metal soap for the purpose of water repellency enhancement is 0.05-5 weight % based on the weight of the formulation. The most preferred metal soap is zinc carboxylate formed by in situ reaction of zinc carbonate and linseed fatty acid.

Other additives can be used in the wood preservative compositions of the present invention. For example, the compositions can further comprise a colorant, a UV stabilizer, a corrosion inhibitor, a water repellent, an anti-foaming agent, or any combination of these. Water can also be added to the wood preservative composition of the present invention, and is preferably present in the water phase of an emulsion concentrate.

When a wax is present in the organic phase, the particle size of the resulting water-dilutable emulsion is typically 100-200 nm, and can depend on the formulation, equipment, and processing conditions (such as homogenization). The emulsions of the present invention exhibit good treatability in wood species such as southern yellow pine and radiata pine. When treating more refractory species such as ponderosa pine, jack pine, and red pine, the treating process described in U.S. Pat. No. 6,274,199 is preferred.

When treatment of a wood species such as Douglas fir is desired, a smaller particle size of the resulting water-dilutable emulsion is preferred. The organic preservatives can be dissolved in mixtures of organic acids and natural oils, alkyd resins, or synthetic esters, and optionally cross-linking catalysts as described above, and mixed with emulsifiers to obtain emulsifiable concentrates. Upon dilution with water, micro-emulsions are formed which have a particle size of <100 nm. These wax-free formulations have many of the benefits and advantages of the wax-containing formulations described above, except for a reduction in water repellency.

When a wax is present in the organic phase, water can be added to form a water-dilutable macro-emulsion concentrate. The percentage of water in the formulation is typically 30-70 weight %, more preferably 50-65 weight % based on the weight of the formulation. Wax, a solubility-enhancing agent, an acid, an organic preservative, and other optional additives are generally heated until all the solids are completely dissolved or molten. The preferred operating temperature is 40-90° C. When the solids are completely dissolved or molten, hot water is added under agitation to form a pre-emulsion which is then further processed to a conventional emulsion using a homogenizer (for example, an APV Gaulin homogenizer). The pre-emulsion can be prepared by using a high-shear mixer. Ideally, the pre-emulsion is maintained at 60-85° C. before using the homogenizer. The emulsion concentrate from the homogenizer can be cooled to ambient temperature using a heat exchanger.

When the organic phase contains a natural oil, a synthetic ester, or a mixture of these, the compositions of the present invention can be formulated as an emulsifiable concentrate, and further diluted with water to form a micro-emulsion before use.

The acids of the current invention include but are not limited to synthetic or natural carboxylic acids, sulfonic acids, or phosphonic acids. Examples of natural carboxylic acids are oleic acid, linoleic acid, linolenic acid, and acid mixtures derived from natural oils such as linseed fatty acid and soy fatty acid. Examples of synthetic acids are 2-ethylhexanoic acid, benzoic acid, dodecylbenzenesulfonic acid, acrylic acid, and methacrylic acid. The preferred acids are the polymerizable acids containing carbon-carbon double bonds. When natural oils or alkyd resins are used as the solubility enhancing agent, the most preferred acids are the unsaturated natural acids or their mixtures since the acids are cross-linked under the same conditions as the solubility enhancing agents. On the other hand, when unsaturated esters such as acrylates and methacrylates are used as the solubility enhancing agents, the most preferred acids are acrylic or methacrylic acid. The concentration of the acids can be 0.1-15%, more preferably 0.5-10%, based on the weight of the formulation.

EXAMPLES

The invention is illustrated but not limited by the following examples.

Example 1

The following example illustrates the preparation of an emulsion (macro-emulsion) formulation using Tebuconazole as a fungicide and Imidacloprid as an insecticide. Linseed oil (Archer Daniels Midland Company) was used as the solubility enhancing agent and linseed fatty acid as the acid. Zinc-linseed fatty acid soap, formed through in situ reaction of zinc carbonate and linseed fatty acid, was used to further improve the water repellency of the formulation.

| Ingredient Name | Function | % w/w |
|---|---|---|
| Ethox CO-40 | Emulsifier | 6.4 |
| DDBSA-IPA | Emulsifier | 1.2 |
| Slack wax | Water repellent | 18.64 |
| Linseed oil | Solubility enhancing agent | 10.13 |
| Linseed fatty acid | Acid | 2.12 |
| Tebuconazole | Fungicide | 1.35 |
| Imidacloprid | Insecticide | 0.027 |
| Zinc carbonate | Water repellent component | 0.14% |
| Water | Dilutant | Balance |

Ethox CO-40 is ethoxylated castor oil with 40 moles of ethylene oxide supplied by Ethox Chemicals, LLC. DDBSA-IPA is the isopropylamine salt of dodecylbenzenesulfonic acid and serves as an anionic surfactant in this formulation. After mixing at 60-85° C. and homogenization in an APV Gaulin homogenizer, the composition is a milky white emulsion having a particle size of 100-250 nm.

Example 2

The following example illustrates the dissolution of Tebuconazole fungicide and Imidacloprid insecticide in a mixture of polymerizable ester, acid, and surfactants to form a clear and transparent emulsifiable concentrate. Upon dilution with water, a transparent micro-emulsion is obtained. The micro-emulsion has a particle size of less than 50 nm.

| Ingredient Name | Function | % w/w |
|---|---|---|
| Tebuconazole | Fungicide | 17.58 |
| Imidacloprid | Insecticide | 0.35 |
| Acrylic acid | Acid | 4.11 |
| Ethyl acrylate | Organic phase/Solubility enhancing agent | 28.54 |
| NP-15 | Emulsifier | 16.98 |
| DDBSA-Na, 22% | Emulsifier | 32.40 |
| AIBN | Radical initiator | 0.04 |

NP-15 is a non-ionic surfactant, which is ethoxylated nonylphenol with 15 moles of ethylene oxide. DDBSA-Na 22% is a 22% solution of sodium dodecylbenzenesulfonate in water. AIBN is 2,2'-azobisisobutyronitrile.

Example 3

The following example illustrates an emulsion prepared as in example 1 with the exception of adding manganese carbonate to form the carboxylate that acts as a cross-linking catalyst. Zinc carboxylate has limited activity as a cross-linking catalyst and it is used mainly as a water repellent.

| Ingredient Name | Function | % w/w |
|---|---|---|
| Ethox CO-40 | Emulsifier | 6.4 |
| DDBSA-IPA | Emulsifier | 1.2 |
| Slack wax | Water repellent | 18.64 |
| Linseed oil | Solubility enhancing agent | 10.13 |

-continued

| Ingredient Name | Function | % w/w |
|---|---|---|
| Linseed fatty acid | Acid | 2.12 |
| Tebuconazole | Fungicide | 1.35 |
| Imidacloprid | Insecticide | 0.027 |
| Zinc carbonate | Water repellent | 0.14% |
| Manganese carbonate | Catalyst | 0.0023% |
| Water | Dilutant | Balance |

Example 4

The following example illustrates the use of a composition of the present invention in a vacuum-pressure treatment process. The emulsion concentrate obtained from Example 1, which contains about 1.35% active Tebuconazole, is diluted with water to 0.05-0.1% active Tebuconazole. The diluted solution is ready to use by vacuum-pressure processes known to those skilled in the wood treating art. The solution can be used at a temperature between 1-99° C., preferably between ambient and about 80° C. Wood species such as southern yellow pine and ponderosa pine can have a solution uptake of 400-700 kg/m$^3$, and virtually full sapwood penetration can be achieved. The composition of the present example can be used with other wood treatment processes such as dipping, brushing, or double vacuum.

Example 5

The following example illustrates the effect of a formulation of the present invention on the leaching resistance of organic preservatives, using Tebuconazole as an example. The composition of Example 1 was compared with a typical emulsifiable concentrate formulation where Tebuconazole was dissolved in oxygenated solvents and mixed with typical anionic-nonionic emulsifiers. The leaching procedure was a modified method based on AWPA Standard Method E-11, in which 19 mm cubes of treated wood are immersed in water for 14 days and the total preservative leached calculated. The wood species used was ponderosa pine. The water repellent (WR) additive of this example was a wax emulsion containing linseed oil and linseed fatty acid.

| Preservative formulation | Additive | % Tebuconazole leaching |
|---|---|---|
| Tebuconazole EC | None | 15.6 |
| Tebuconazole EC | WR, 1.8% in treating solution | 10.6 |
| Example 1 | None | 5.6 |

Example 6

The following example illustrates the improvement in preservative distribution gradient when using the formulations of the present invention. The effect on Tebuconazole preservative concentration distribution in different zones of treated wood was analyzed as a function of different formulations. End-matched ponderosa pine boards measuring 40×72×152 mm were end-sealed with epoxy paint and treated with different formulations. All treating solutions had 700 PPM active Tebuconazole and 1.5% water repellent. The boards were treated using a typical modified full-cell vacuum-pressure treatment process consisting of an initial vacuum period of 5 minutes at a vacuum 16 inches (40.64 cm) Hg, a pressure period of 60 minutes at 150 PSI (1.03 MPa), and a final vacuum period of 20 minutes (a vacuum) at a vacuum of 26 inches (66.04 cm) Hg. Because of natural variations in wood, five replicate boards were treated and analyzed to obtain meaningful averaged results. After treatment and drying, a 12 mm thick wafer was cut from each of the 152 mm long boards and the cross-section of the 12 mm thick wafers were sectioned into three zones of equal cross-sectional area. The Tebuconazole concentration ratio in the three zones was used as a measure of preservative distribution gradient. The effect of selected small molecular weight compounds on Tebuconazole distribution gradient was also studied. These are nitrogen-containing compounds having similar pKb as that of Tebuconazole.

| Preservative Formulation | Additive | Outer/middle/inner zone ratio |
|---|---|---|
| Tebuconazole EC | None | 1:0.45:0.27 |
| Example 1 | — | 1:0.71:0.55 |
| Tebuconazole EC | 0.051% 1,2,4-triazole | 1:0.57:0.40 |
| Tebuconazole EC | 0.059% pyridazine | 1:0.56:0.38 |
| Tebuconazole EC | 0.071% N-methylpyrrolidone | 1:0.59:0.38 |

The formulation described in Example 1 provided the most desirable Tebuconazole distribution gradient. In addition, the nitrogen-containing additives also worked well. Without being bound by any particular theory, it is believed that the nitrogen-containing small molecules compete with triazole preservatives, such as Tebuconazole, for active binding sites in wood and therefore flatten the distribution gradient. It is also believed that the improved distribution gradient is due in part to a reduced interaction between the active preservative and the wood, which probably results from the presence of acids and solubility enhancing agents.

Example 7

The following example examines the water repellency of select compositions of the present invention. The formulations in Examples 1 and 3 were chosen because they have both an active preservative and a water repellent component. Therefore, the water repellency of the formulations of example 1 and 3 was compared with conventional preservative formulations also having a water repellent component at the same levels. The water repellency was measured by anti-swelling efficiency as defined in WDMA (Window and Door Manufacturers' Association) Standard Test Method TM-2. Instead of treating wood wafers as in TM-2, the test wafers were cut from large dimension treated boards in this study. The water repellent of this example is a wax-based emulsion.

| Preservative formulation | Water repellent | Anti-swelling efficiency (%) |
|---|---|---|
| Tebuconazole EC | 1.54% | 44.7% |
| Example 1 without Zn | Built-in | 71.0% |
| Example 3 | Built-in | 75.0% |

The positive effect of metals on water repellency is also illustrated in this example. The formulation of Example 1 without zinc carbonate had a lower water repellency than Example 3.

What is claimed is:

1. A wood preservative composition comprising:
   an organic preservative agent that is not a quaternary ammonium compound, and an organic acid, solubilized in an organic phase essentially free of volatile organic compounds; and
   an emulsifier comprising a combination of a non-ionic surfactant and an anionic surfactant comprising a salt of dodecylbenzenesulfonic acid;
   the composition being dilutable with water to form the organic phase of an emulsion.

2. The wood preservative composition according to claim 1, in which said organic preservative agent comprises 3-Iodo-2-propynyl butyl carbamate, chlorothalonil, an isothiazolone, a triazole, or a combination of these.

3. The wood preservative composition according to claim 1, in which said organic preservative agent comprises Propiconazole, Tebuconazole, Hexaconazole, Cyproconazole, Dinaconazole, or a combination of these.

4. The wood preservative composition according to claim 1, in which said organic acid comprises oleic acid, linoleic acid, linolenic acid, an acid combination derived from a natural oil, 2-ethylhexanoic acid, benzoic acid, acrylic acid, methacrylic acid, or a combination of these.

5. The wood preservative composition according to claim 1, in which said organic phase comprises a hydrophobe.

6. The wood preservative composition according to claim 1, in which said organic phase comprises a wax.

7. The wood preservative composition according to claim 1, in which said non-ionic surfactant comprises ethoxylated nonylphenol, ethoxylated alcohol, ethoxylated castor oil, or a combination of these.

8. The wood preservative composition according to claim 1, in which said composition further comprises a preservative solubilizing agent, present in an amount effective to increase the solubility of said preservative in said organic phase.

9. The wood preservative composition according to claim 1, in which said composition further comprises a free radical initiator.

10. The wood preservative composition according to claim 1, in which said composition further comprises a small molecular weight (molecular weight<200) nitrogen-containing compound.

11. The wood preservative composition according to claim 1, in which said composition further comprises a metal soap cross-linking catalyst.

12. The wood preservative composition according to claim 1, free of volatile organic compounds.

13. A wood preservative composition comprising:
   an organic preservative agent that is not a quaternary ammonium compound, and an organic acid, solubilized in an organic phase essentially free of volatile organic compounds; and
   a preservative solubilizing agent comprising linseed oil, tung oil, fish oil, or a combination of these, present in an amount effective to increase the solubility of said preservative in said organic phase;
   the composition being dilutable with water to form the organic phase of an emulsion.

14. The wood preservative composition according to claim 13, in which said organic preservative agent comprises 3-Iodo-2-propynyl butyl carbamate, chlorothalonil, an isothiazolone, a triazole, or a combination of these.

15. The wood preservative composition according to claim 13, in which said organic preservative agent comprises Propiconazole, Tebuconazole, Hexaconazole, Cyproconazole, Dinaconazole, or a combination of these.

16. The wood preservative composition according to claim 13, in which said organic acid comprises oleic acid, linoleic acid, linolenic acid, an acid combination derived from a natural oil, 2-ethylhexanoic acid, benzoic acid, acrylic acid, methacrylic acid, or a combination of these.

17. The wood preservative composition according to claim 13, in which said organic phase comprises a hydrophobe.

18. The wood preservative composition according to claim 13, in which said organic phase comprises a wax.

19. The wood preservative composition according to claim 13, further comprising an emulsifier.

20. The wood preservative composition according to claim 13, in which said composition further comprises a preservative solubilizing agent, present in an amount effective to increase the solubility of said preservative in said organic phase.

21. The wood preservative composition according to claim 13, in which said composition further comprises a free radical initiator.

22. The wood preservative composition according to claim 13, in which said composition further comprises a small molecular weight (molecular weight<200) nitrogen-containing compound.

23. The wood preservative composition according to claim 13, in which said composition further comprises a metal soap cross-linking catalyst.

24. The wood preservative composition according to claim 13, free of volatile organic compounds.

25. A wood preservative composition comprising:
   an organic preservative agent that is not a quaternary ammonium compound, and an organic acid, solubilized in an organic phase essentially free of volatile organic compounds, and
   an organic biocide that comprises an insecticide that comprises Imidacloprid, Cyfluthrin, or a combination of these, or a combination of said insecticide and a mold inhibitor
   the composition being dilutable with water to form the organic phase of an emulsion.

26. The wood preservative composition according to claim 25, in which said organic preservative agent comprises 3-Iodo-2-propynyl butyl carbamate, chlorothalanil, an isothiazolone, a triazole, or a combination of these.

27. The wood preservative composition according to claim 25, in which said organic preservative agent comprises Propiconazole, Tebuconazole, Hexaconazole, Cyproconazole, Dinaconazole, or a combination of these.

28. The wood preservative composition according to claim 25, in which said organic acid comprises a carboxylic acid, a sulfonic acid, a phosphonic acid, or a combination of these.

29. The wood preservative composition according to claim 25, in which said organic acid comprises oleic acid, linoleic acid, linolenic acid, an acid combination derived from a natural oil, 2-ethylhexanoic acid, benzoic acid, acrylic acid, methacrylic acid, or a combination of these.

30. The wood preservative composition according to claim 29, in which said natural oil derived acid comprises linseed fatty acid, soy fatty acid or a combination of these.

31. The wood preservative composition according to claim 25, in which said organic phase comprises a hydrophobe.

32. The wood preservative composition according to claim 25, in which said organic phase comprises a wax.

33. The wood preservative composition according to claim 25, in which said organic phase comprises petroleum wax, a natural wax, a synthetic wax, oxidized polyethylene wax, or a combination of these.

34. The wood preservative composition according to claim 25, in which said organic phase comprises slack wax, microcrystalline wax, or a combination of these.

35. The wood preservative composition according to claim 25, further comprising an emulsifier.

36. The wood preservative composition according to claim 35, in which said emulsifier comprises a combination of a non-ionic surfactant and an anionic surfactant.

37. The wood preservative composition according to claim 36, in which said non-ionic surfactant comprises ethoxylated nonylphenol, ethoxylated alcohol, ethoxylated castor oil, or a combination of these.

38. The wood preservative composition according to claim 37, in which said non-ionic surfactant comprises ethoxylated castor oil having an HLB of at least 12.

39. The wood preservative composition according to claim 25, in which said composition further comprises a preservative solubilizing agent, present in an amount effective to increase the solubility of said preservative in said organic phase.

40. The wood preservative composition according to claim 39, in which said preservative solubilizing agent comprises a natural oil.

41. The wood preservative composition according to claim 25, in which said composition further comprises a free radical initiator.

42. The wood preservative composition according to claim 41, in which said free radical initiator comprises a thermocleavable initiator, a redox initiator, or a combination of these.

43. The wood preservative composition according to claim 41, in which said free radical initiator comprises AIBN (2,2'-azobisisobutyronitrile), potassium persulfate, or a combination of these.

44. The wood preservative composition according to claim 25, in which said composition further comprises a small molecular weight (molecular weight<200) nitrogen-containing compound.

45. The wood preservative composition according to claim 44, in which said nitrogen-containing compound comprises 1,2,4-triazole.

46. The wood preservative composition according to claim 44, in which said nitrogen-containing compound is present at a concentration effective for improving the chemical distribution gradient in a treated wood product.

47. The wood preservative composition according to claim 25 in which said composition further comprises a metal soap cross-linking catalyst.

48. The wood preservative composition according to claim 47, in which said metal soap cross-linking catalyst is present at a concentration effective for drying an oil.

49. The wood preservative composition according to claim 25, further comprising zinc (II) in the form of a carbonate, a hydroxide, an oxide, a carboxylate, or a combination of these.

50. The wood preservative composition according to claim 25, in which said composition further comprises a colorant, a UV stabilizer, a corrosion inhibitor, a water repellent, an anti-foam, or a combination of these.

51. The wood preservative composition according to claim 25, free of volatile organic compounds.

* * * * *